(12) United States Patent
Serre et al.

(10) Patent No.: US 7,445,903 B2
(45) Date of Patent: Nov. 4, 2008

(54) FIBRIN CITRULLINE DERIVATIVES AND THEIR USE FOR DIAGNOSING OR TREATING RHEUMATOID ARTHRITIS

(75) Inventors: Guy Serre, Toulouse (FR); Mireille Sebbag, Toulouse (FR)

(73) Assignee: Biomerieux SA, Marcy l'Etoile (FR)

( * ) Notice: Subject to any disclaimer, the term of this patent is extended or adjusted under 35 U.S.C. 154(b) by 198 days.

(21) Appl. No.: 11/339,548

(22) Filed: Jan. 26, 2006

(65) Prior Publication Data

US 2007/0009507 A1   Jan. 11, 2007

Related U.S. Application Data

(63) Continuation of application No. 10/019,439, filed as application No. PCT/FR00/01857 on Jun. 30, 2000, now Pat. No. 7,022,485.

(30) Foreign Application Priority Data

Jul. 1, 1999   (FR) .................................. 99 08470

(51) Int. Cl.
  *C12Q 1/68*   (2006.01)
  *A61K 38/04*   (2006.01)

(52) U.S. Cl. ........................ 435/7.1; 530/327; 530/328; 530/329; 530/330; 530/380

(58) Field of Classification Search ........................ None
  See application file for complete search history.

(56) References Cited

U.S. PATENT DOCUMENTS

| 2,520,733 | A | 8/1950 | Rupert et al. |
| 3,188,353 | A | 6/1965 | Holtschmidt |
| 3,326,985 | A | 6/1967 | Mason |
| 4,281,061 | A | 7/1981 | Zuk et al. |
| 4,551,561 | A | 11/1985 | Stuehler |
| 5,403,912 | A | 4/1995 | Gunatillake et al. |
| 5,616,679 | A | 4/1997 | Fies et al. |
| 5,659,089 | A | 8/1997 | Cai et al. |
| 5,821,068 | A | 10/1998 | Soe et al. |
| 5,858,723 | A | 1/1999 | Mueller-Lantzsch et al. |
| 7,022,485 | B1 * | 4/2006 | Serre et al. .................. 435/7.1 |
| 2002/0007043 | A1 | 1/2002 | Sunkara et al. |

FOREIGN PATENT DOCUMENTS

| WO | 92/09647 | 6/1992 |
| WO | 95 28946 | 11/1995 |
| WO | 98 22503 | 5/1998 |
| WO | 01/44150 A2 | 6/2001 |
| WO | 01/44348 A1 | 6/2001 |

OTHER PUBLICATIONS

Masson-Bessiere et al. Synovial target antigens of antifilaggrin auto antibodies are deiminated froms of fibrin alpha and beta chains. Revue Du Rhumatisme, 66:754, Dec. 1999.

Tarcsa et al. Protein unfolding by peptidylarginine deiminase. Substrate specificity and structural relationships of the natural substrates trichohyalin and filaggrin. J Biol Chem. 271(48):307016, 1996.

Schellekens et al. Citrulline is an essential constituent of antigenic determinants recognized by rheumatoid arthritis-specific autoantibodies. J Clin Invest. 101(1):273-281. 1998.

* cited by examiner

*Primary Examiner*—Maher M Haddad
(74) *Attorney, Agent, or Firm*—Oblon, Spivak, McClelland, Maier & Neustadt, P.C.

(57) ABSTRACT

The invention concerns citrulline polypeptide derived from fibrin useful for diagnosing or treating rheumatoid arthritis.

16 Claims, 3 Drawing Sheets

FIBRIN CITRULLINE DERIVATIVES AND THEIR USE FOR DIAGNOSING OR TREATING RHEUMATOID ARTHRITIS

CROSS-REFERENCE TO RELATED APPLICATIONS

The present application is a continuation of U.S. application Ser. No. 10/019,439 filed May 8, 2002, U.S. Pat. No. 7,022,485, which is a 371 application of PCT/FR00/01857 filed Jun. 30, 2000.

The present invention relates to citrullinated derivatives of fibrin and to their uses in diagnosing and treating rheumatoid arthritis.

Rheumatoid arthritis (hereinafter abbreviated to "RA") is the most common of the forms of chronic inflammatory rheumatism. It is an autoimmune disease; the serum of affected patients contains autoantibodies, some of which are specific and may constitute a marker for this disease, allowing it to be diagnosed even at early stages.

Prior studies by the team of the inventors have shown that these antibodies recognize different molecular forms of the (pro)filaggrin family (for review, cf. for example SERRE and VINCENT, In: Autoantibodies, PETER and SHOENFIELD Eds, Elsevier Science Publishers, 271 276, 1996). These antibodies have, for this reason, been named: "antifilaggrin autoantibodies (AFAs)". Application EP 0 511 116 describes the purification and characterization of antigens of the filaggrin family, recognized by these antibodies, and their use for diagnosing rheumatoid arthritis.

The inventors have shown that the epitopes recognized by the AFAs are carried by regions of the filaggrin molecule, in which at least some of the arginines are deiminated and thus transformed into citrulline; citrullinated peptides specifically recognized by AFAs have thus been obtained from the main immunoreactive regions of filaggrin. These peptides, and their use for diagnosing RA, are the subject of Application PCT/FR97/01541 and of Application PCT/FR98/02899 in the name of BIOMERIEUX. The inventors' observations concerning the role of citrulline residues in the reactivity of filaggrin with RA-specific autoantibodies have subsequently been confirmed by other researchers [SCHELLEKENS et al., Arthritis Rheum., 40, no. 9 supplement, p. S276, summary 1471 (1997); VISSER et al., Arthritis Rheum., 40, no. 9 supplement, p. S289, summary 1551 (1997)].

The inventors have also shown that AFAs represent a considerable proportion of the interstitial immunoglobulins of synovial rheumatoid tissues and that they are synthesized locally by specific plasmocytes present in these tissues, which confirms the hypothesis that they are involved in the autoimmune response associated with RA. The use of filaggrin, or of citrullinated peptides derived therefrom, to neutralize this autoimmune response is the subject of Application PCT/FR98/02900 in the name of UNIVERSITE PAUL SABATIER [Paul Sabatier University] (TOULOUSE III).

However, the involvement of filaggrin as an immunogen or as a target antigen in the autoimmune response associated with RA has never been noted. The true antigen involved in this response remains to be identified.

The inventors have now succeeded in characterizing this antigen and have thus shown that it is composed of citrullinated derivatives of the α- and/or β-chains of fibrin.

A subject of the present invention is a citrullinated polypeptide derived from all or part of the sequence of the α-chain or of the β-chain of a vertebrate fibrin, by substitution of at least one arginine residue with a citrulline residue.

Preferably, a polypeptide in accordance with the invention comprises at least 5 consecutive amino acids and advantageously at least 10 consecutive amino acids, including at least one citrulline, of the sequence of the α-chain or of the β-chain of a mammalian fibrin. Advantageously, said vertebrate fibrin is a mammalian fibrin, preferably a human fibrin.

Citrullinated polypeptides in accordance with the invention may, for example, be obtained from natural, recombinant or synthetic fibrin or fibrinogen, or from fragments thereof, comprising at least one arginine residue, by the action of peptidyl arginine deiminase (PAD); they may also be obtained by peptide synthesis, directly incorporating one or more citrulline residues into the synthesized peptide.

Citrullinated polypeptides in accordance with the invention may also be pseudopeptides having the same three-dimensional structure, and therefore the same immunological reactivity, as the citrullinated polypeptides derived from the α- or β-chains of fibrin, or from fragments thereof, mentioned above. They may, for example, be pseudopeptides of the retro type, in which L-amino acids are linked together according to a reverse sequence of that of the peptide to be reproduced, or pseudopeptides of the retro-inverso type, consisting of D-series amino acids (instead of the L-series amino acids of natural peptides) linked together according to a reverse sequence of that of the peptide to be reproduced, or alternatively pseudopeptides containing a $CH_2$-NH bond in place of a CO—NH peptide bond. Pseudopeptides of these various types are, for example, described by BENKIRANE et al. [J. Biol. Chem., 270, p. 11921 11926, (1995); J. Biol. Chem., 271, p. 33218 33224, (1996)]; BRIAND et al. [(J. Biol. Chem., 270, p. 20686 20691, (1995); GUICHARD et al. [J. Biol. Chem., 270, p. 26057 26059, (1995)].

AFAP=purified AFAs;
RA sera=rheumatoid sera:
*AFA+=AFA-positive;
*AFA−=AFA-negative;
control sera =sera derived from patients suffering from forms of inflammatory rheumatism other than RA, or from healthy donors.

Figure 2:
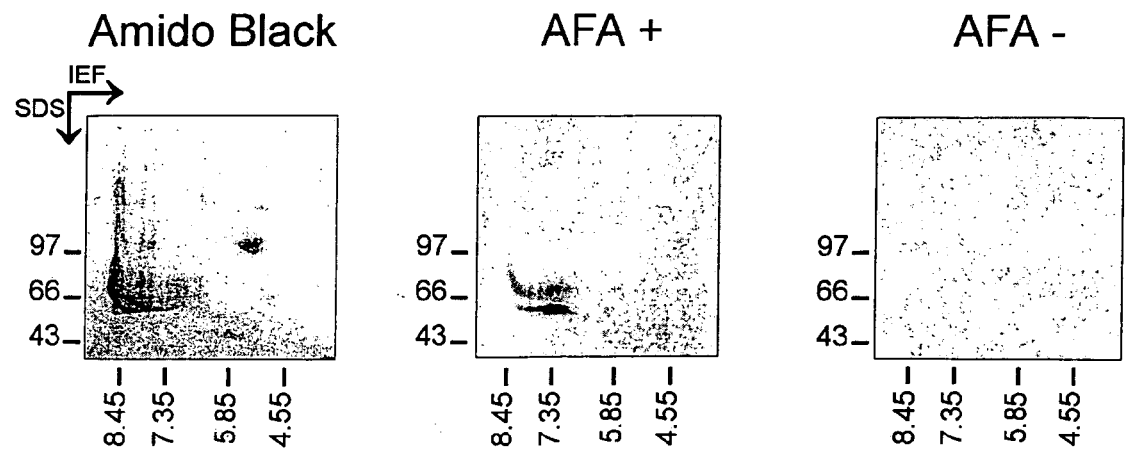

FIG. 2 illustrates the profiles obtained after electrotransfer onto a PVDF membrane and:
a) staining with amido black; or
b) immunodetection with an AFA-positive rheumatoid serum; or
c) immunodetection with an AFA-negative rheumatoid serum.

Amido Black =staining with amido black;
AFA+=immunodetection with an AFA-positive rheumatoid serum;
AFA−=immunodetection with an AFA-negative rheumatoid serum.

Figure 3A:
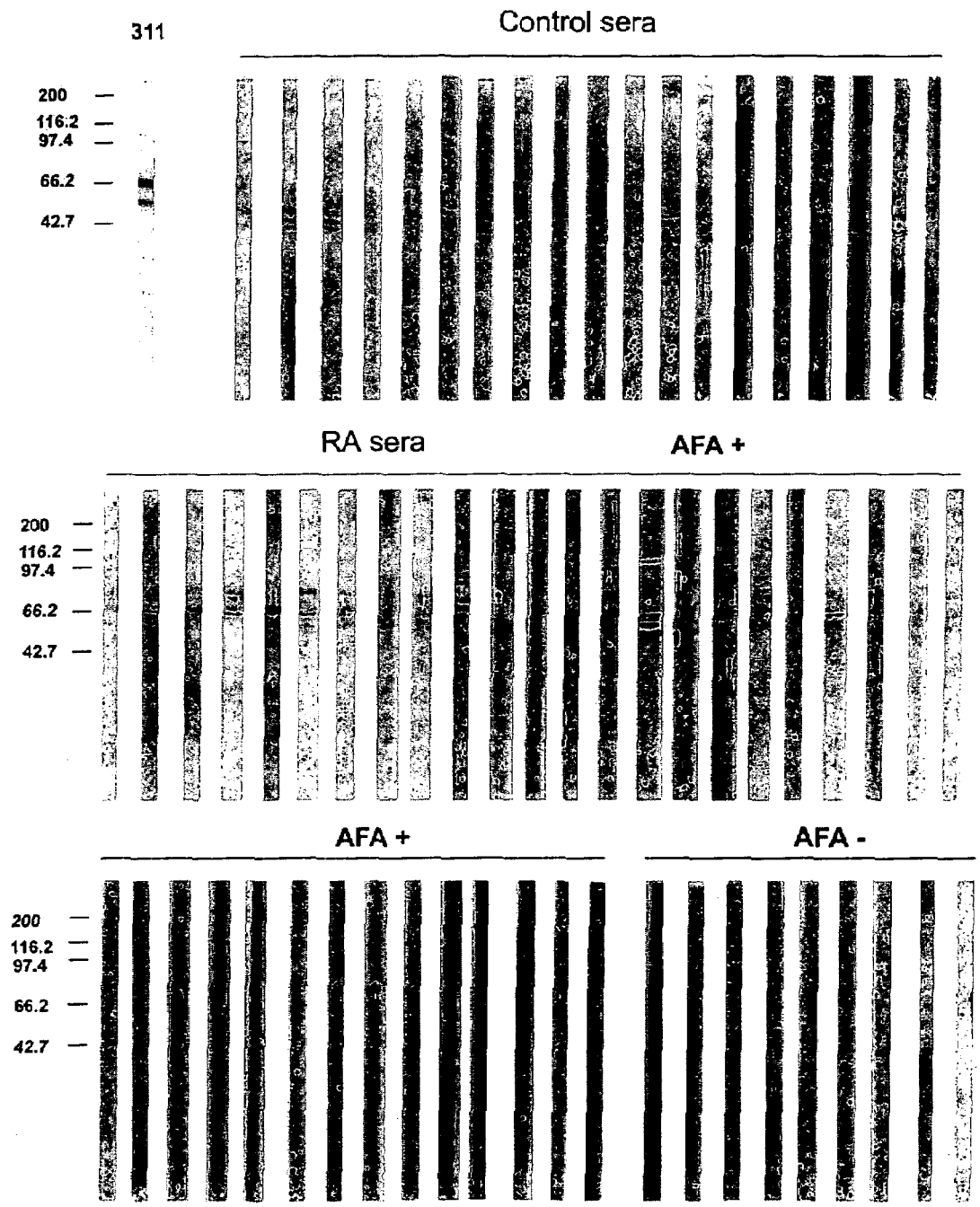

FIG. 3(A) shows reactivity with respect to deiminated and nondeiminated fibrinogen was studied by immunotransfer in the case of nondeiminated fibrinogen and (B) in the case of deiminated fibrinogen.

Figure 3B:
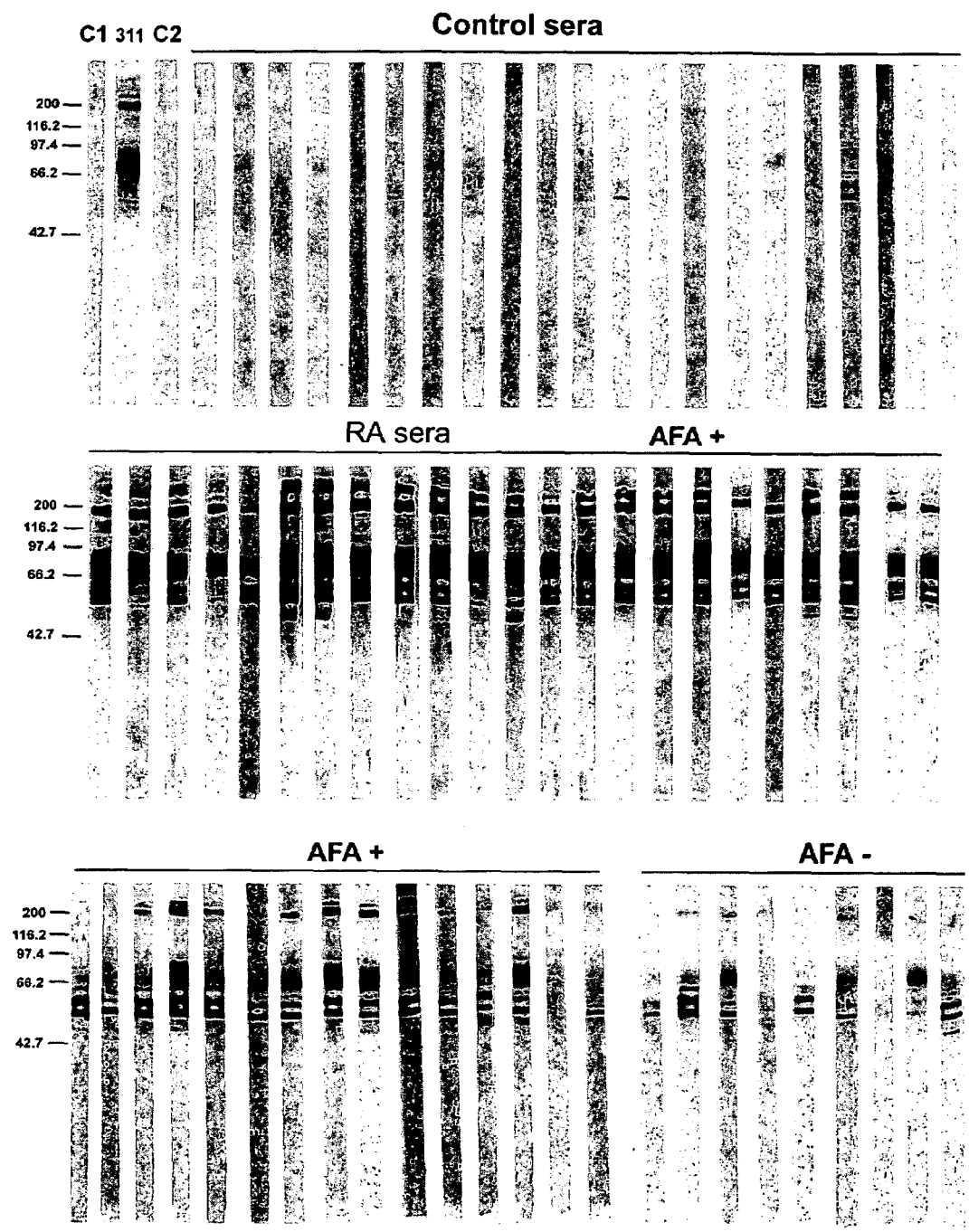

FIG. 3A: non deiminated purified human fibrmogen;
311 =antifibrinogen monoclonal antibody 311;
control sera =sera derived from patients suffering from forms of inflammatory rheumatism other than RA, or from healthy donors;

RA sera =rheumatoid sera;
* AFA+=AFA-positive;
* AFA−=AFA-negative;

FIG. 3B: purified human fibrinogen deiminated with a PAD;
311 =antifibrinogen monoclonal antibody 311;
C1 =sheep antibody directed against mouse IgGs;
C2 sheep antibody directed against protein A;
control sera =sera derived from patients suffering from forms of inflammatory rheumatism other than RA, or from healthy donors;
RA sera rheumatoid sera;
*AFA+=AFA-positive;
*AFA−=AFA-negative;

A subject of the present invention is also the use of the polypeptides in accordance with the invention, as defined above, for diagnosing RA, in vitro.

The present invention in particular encompasses antigenic compositions for diagnosing the presence of RA-specific autoantibodies in a biological sample, which compositions are characterized in that they contain at least one polypeptide in accordance with the invention, optionally labeled with and/or conjugated to a carrier molecule.

A subject of the present invention is also a method for detecting RA-specific autoantibodies of the G class in a biological sample, which method is characterized in that it comprises: bringing said biological sample into contact with at least one polypeptide in accordance with the invention, as defined above, under conditions which allow the formation of an antigen/antibody complex with the RA-specific autoantibodies possibly present; detecting, by any suitable means, the antigen/antibody complex possibly formed.

This detection method may be carried out using a kit comprising at least one antigen according to the invention, and also buffers and reagents suitable for constituting a reaction medium which allows the formation of an antigen/antibody complex, and/or means for detecting said antigen/antibody complex.

Said kit may also comprise, where appropriate, reference samples, such as one or more negative serum (sera) and one or more positive serum (sera).

A subject of the present invention is also the use of citrullinated polypeptides in accordance with the invention, for producing a medicinal product, and especially a medicinal product intended to neutralize the autoimmune response associated with RA, and in particular to inhibit the attachment of the humoral or cellular effectors of this autoimmune response, to the citrullinated derivatives of α- or β-chains of fibrin which are present in rheumatoid tissues.

This in vivo neutralization of the autoimmune response may contribute to treating RA or other diseases which are thought to involve lesions induced by an autoimmune response directed against epitopes exhibiting cross-reactions with the citrullinated derivatives of α- or β-chains of fibrin.

Advantageously, for in vivo administration, polypeptides modified so as to prolong their lifetime in the organism, in particular by increasing their resistance to proteases, will be chosen; they may in particular be pseudopeptides, such as those mentioned above.

The present invention also encompasses pharmaceutical compositions, in particular for treating rheumatoid arthritis, characterized in that they contain, as active principle, at least one polypeptide in accordance with the invention.

Pharmaceutical compositions in accordance with the invention may be administered by any suitable means known per se. They may, for example, be administered systemically, orally, parenterally, or by subcutaneous, intravenous or intramuscular injection; they may also be administered locally, for example by intra-articular injections or by microinjections, under arthroscopy, into the inflammatory synovial tissue.

The present invention will be more clearly understood using the additional description which follows, which refers to the identification of deiminated forms of the α-chain or β-chain of human fibrin in rheumatoid tissues, and to the use of deiminated fibrinogen for detecting the presence of AFAs in serum samples.

EXAMPLE 1

Purification and Characterization of Antigenic Proteins Recognized by AFAs in Rheumatoid Synovial Tissues 1) Analysis of Rheumatoid Synovial Tissues
Materials and Methods:

The synovial tissue samples used for the protein extractions were taken from patients suffering from rheumatoid arthritis, during a synovectomy or an arthroplasty of the wrist or knee, and all correspond to tissue fragments which are the seat of conventional histological rheumatoid synovitis lesions. They are conserved by freezing in isopentane cooled with liquid nitrogen.

Synovial tissue fragments originating from four patients were extracted sequentially, in a low ionic strength buffer, a urea buffer and in a urea/DTT buffer, successively.

Preparation of Synovial Extracts

The extraction was carried out using an Ultra-Turrax homogenizer (T25 basic, IKA Labortechnik, Staufen, Germany) with a volume of 6 ml of buffer per gram of tissue.

The following buffers were used at a temperature of 0° C.: 40 mM Tris-HCl, pH 7.4, containing 150 mM of NaCl [low ionic strength buffer]; 40 mM Tris-HCl, pH 7.4, containing 8M urea deionized on an ion exchange resin (AG 501-X8, Biorad, Hercules, Calif.) [urea buffer]; 40 mM Tris-HCl, pH 7.4, containing 8M deionized urea and 50 mM dithiothreitol (DTT), (Sigma) [urea/DTT buffer]. All the buffers were supplemented with 20 mM EDTA, 0.02% sodium azide, 2 µg/ml aprotinin, 10 mM N-ethylmaleimide and 1 mM phenylmethylsulfonyl fluoride (Sigma, Saint Louis, Mich.). After each extraction, the homogenates were centrifuged for 20 minutes at 15,000 g, at the temperature of 4° C. The urea buffer and urea/DTT buffer extracts were dialyzed against water before being analyzed by electrophoresis and by immunotransfer.

Electrophoresis and Immunodetection

The synovial proteins of the various extracts were separated by electrophoresis on a 10% polyacrylamide gel in denaturing SDS buffer (SDS-PAGE), and were then electrotransferred onto reinforced nitrocellulose membranes (Hybond-™C extra, Amersham, Little Chalfont, UK).

The membranes were immunodetected with the following antibody preparations; AFA-positive or AFA-negative rheumatoid human sera; non-rheumatoid control human sera derived from patients suffering from other forms of inflammatory rheumatism or from healthy individuals (1/100); purified fractions of AFAs (10 µg/ml); mouse monoclonal antibody directed against human fibrin and fibrinogen (5 µg/ml); two sheep antisera directed, respectively, against recombinant α- and γ-chains of human fibrinogen (1/1000) (Cambio, Cambridge, UK); a rabbit antiserum directed against the recombinant β-chain of human fibrinogen (1/200000) (Cambio).

The human sera used are derived from 95 patients suffering from rheumatoid arthritis (RA), perfectly characterized from a clinical and biological point of view according to the criteria of the American College of Rheumatology, from 24 patients suffering from non-rheumatoid inflammatory rheumatism or from non-inflammatory pathological conditions (control sera) and from 10 healthy individuals. The semi-quantitative titration of the antifilaggrin antibodies (AFAs) in the sera was carried out by indirect imunofluorescence on cryosections of rat esophageal epithelium and by immunotransfer on epidermal extracts enriched in filaggrin acid variant, according to previously published protocols [VINCENT et al., Ann. Rheum. Dis., 48, 712 722 (1989); VINCENT et al., J. Rheumatol., 25, 838 846 (1998)]. The "AFA-positive" sera are those which exhibit AFAs at significant titers after detection using both methods, and the "AFA-negative" sera are those which do not exhibit detectable AFAs by either of the two methods.

The AFAs were purified by affinity chromatography on the epidermal filaggrin acid variant, according to the protocol described by GIRBAL-NEUHAUSER et al. (J. Immunol., 162, 585 594 (1999), using 45 rheumatoid sera having a high AFA titer. The purified antibody fractions were pooled.

Peroxidase-conjugated secondary molecular probes were used for detecting all the primary antibodies: protein A (Sigma), sheep antibodies directed against mouse IgGs (Biosys, Compiegne, France), goat Fab fragments directed against rabbit IgGs (Biosys) and rabbit F(ab')2 fragments directed against sheet IgGs (Southern Biotech. Inc), for detecting, respectively, human, murine, rabbit and sheep IgGs. The peroxidase activity was visualized using the ECL™ detection system (Amersham International, Aylesbury, UK), according to the protocol provided by the manufacturer.

Results

Specific reactivity with the purified AFAs and the AFA-positive rheumatoid sera was observed only in the extract produced in urea/DTT buffer.

Figure 1:
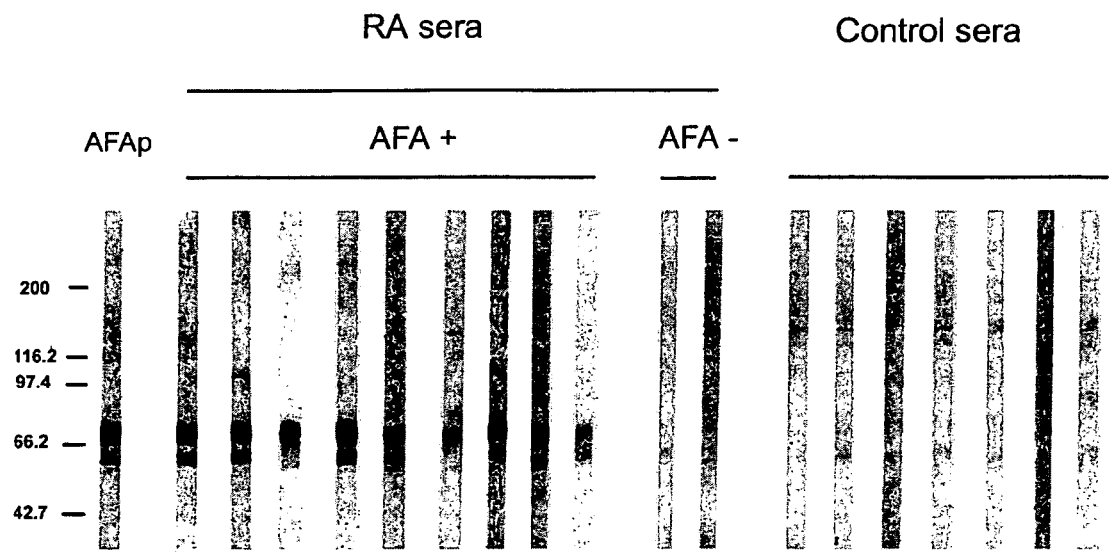
FIG. 1 shows the specific reactivity with the purified AFAs and the AFA-positive rheumatoid sera was observed only in the extract produced in urea/DTT buffer.

The results are illustrated by FIG. 1:

Legend to FIG. 1:
AFAP=purified AFAs;
RA sera=rheumatoid sera:
AFA+=AFA-positive;
AFA-=AFA-negative;
control sera=sera derived from patients suffering from forms of inflammatory rheumatism other than RA, or from healthy donors.

These results show that the specific reactivity with the purified AFAs and the AFA-positive rheumatoid sera relates to two protein bands of apparent molecular weight of approximately 64 kD to approximately 78 kD (w64-78) and of approximately 55 kD to approximately 61 kD (w55-61), respectively. These protein bands were not detected by the AFA-negative sera, regardless of whether they originate from patients suffering from RA or from other forms of inflammatory rheumatism, or are derived from healthy donors.

The presence of these proteins specifically recognized by the purified AFAs and the AFA-positive rheumatoid sera was observed in the urea/DTT extracts of synovial tissues derived from the 4 rheumatoid patients studied.

In total, 48 AFA-positive rheumatoid sera were tested by immunotransfer on at least one synovial urea/DTT extract. Among the sera, 40 recognized w64-78, 39 recognized w55-61, 37 recognized both w64-78 and w55-61, 3 recognized only w64-78 and 2 recognised only w55-61.

Thirteen AFA-negative rheumatoid sera were tested by immunotransfer on at least one urea/DTT extract of synovial tissue; none of these sera recognized either w64-78 or w55-61.

Ten sera derived from healthy donors and 5 sera derived from patients suffering from other forms of inflammatory rheumatism were also tested by immunotransfer on at least one synovial urea/DTT extract; none of these sera recognized either w64-78 or w55-61.

2) Characterization of the w64-78 and w55-61 Antigenic Proteins

The proteins of the urea/DTT buffer extract of the synovial tissue of one of the patients suffering from RA were precipitated with 4 volumes of glacial acetone and then redissolved in the urea/DTT buffer at a concentration 15 times higher than their initial concentration.

The proteins of the concentrated extract were separated by two-dimensional electrophoresis, by isoelectrofocussing followed by SDS-PAGE.

A two-dimensional electrophoretic separation was carried out in the PhastSystem™ (Pharmacia). The first electrophoretic separation was performed on PhastGel™ isoelectrofocussing (IEF) gels which, beforehand, had been washed, dried and rehydrated in a deionized buffer containing 8 M urea, 0.5% Nonidet P-40 and ampholytes creating a pH gradient of 3 to 10 (Pharmacia). The second dimension was performed by SDS-PAGE on 7.5% polyacrylamide gels.

The proteins were then electrotransferred onto polyvinyl difluoride (PVDF) membranes (ProBlott™ membranes, Applied Biosystems, Foster City, Calif.), in 50 mM Tris and 50 mM of boric acid. The membranes were finally stained with an aqueous solution of amido black at 0.1%, of acetic acid at 1% and of methanol at 45%, or immunodetected with rheumatoid sera according to the protocol described in 1) above.

FIG. 2 illustrates the profiles obtained after electrotransfer onto a PVDF membrane and:
a) staining with amido black; or
b) immunodetection with an AFA-positive rheumatoid serum; or
c) immunodetection with an AFA-negative rheumatoid serum.

Legend to FIG. 2:
Amido Black=staining with amido black;
AFA+=immunodetection with an AFA-positive rheumatoid serum;
AFA-=immunodetection with an AFA-negative rheumatoid serum.

After staining with amido black, the presence of two major proteins, with an apparent molecular weight of 64-78 kD and 55-61 kD and pI of approximately 5.85 to approximately 8.45, is observed.

These proteins are immunodetected with the AFA-positive rheumatoid sera but not with the AFA-negative rheumatoid sera.

Using identical transfers onto a PVDF membrane after two-dimensional electrophoresis, membrane fragments corresponding to the center of each immunoreactive zone were excised and then subjected to amino-terminal sequencing in an Applied Biosystems sequencer (494A or 473A), according to the method recommended by the manufacturer.

The sequence gly-pro-arg-val-val-glu-arg-his-gln-ser-ala (SEQ ID NO.1) was obtained from the membrane fragment corresponding to the w64-78 antigen. This sequence is strictly identical to the sequence 36-46 of the product of the human fibrinogen α-chain precursor gene. When membrane fragments corresponding to the right or left ends of the w64-78 immunoreactive zone were excised and then subjected to three cycles of amino-terminal sequencing, gly-proarg sequences were found each time, indicating that the entire p64-78 immunoreactive zone has the same amino-terminal end.

The sequence gly-his-arg-pro-leu-asp-lys-lys-arg (SEQ ID NO.2) was obtained from the membrane fragment corresponding to the center of the immunoreactive zone corresponding to the w55-61 antigen. This sequence is strictly identical to the sequence 45-54 of the product of the human fibrinogen β-chain precursor gene. When a membrane fragment corresponding to the left end of the w55-61 immunoreactive zone was excised and then subjected to two cycles of amino-terminal sequencing, the gly-his sequence was found. When a membrane fragment corresponding to the right end of the w55-61 immunoreactive zone was excised and then subjected to six cycles of amino-terminal sequencing, the gly-his-arg-pro-leu-asp (SEQ ID NO.3) and the gly-pro-arg-val-val-glu (SEQ ID NO.4) sequence were found. This indicates that the entire w55-61 immunoreactive zone has the same amino-terminal end and that it partially co-migrates with the w64-78 antigen.

The amino-terminal ends of the w64-78 and w55-61 antigenic proteins correspond, respectively, to the amino-terminal ends of the α- and β-chains of human fibrinogen after respective cleavage, by thrombin, of fibrinopeptides A and B. The amino-terminal ends of the w64-78 and w55-61 antigenic proteins are therefore identical, respectively, to that of the α-chain and to that of the β-chain of human fibrin.

The apparent molecular weights of the w64-78 and w55-61 antigens are compatible with the respective theoretical molecular weight values for the α-chain and for the β-chain of human fibrin.

The identity of the w64-78 antigen and of the α-chain of fibrin, on the one hand, and that of the w55-61 antigen and of the β-chain of fibrin, on the other hand, were confirmed by analyzing the reactivity of antifibrin(ogen) antibodies with respect to these antigens. By immunotransfer, using an extract of synovial tissue prepared in urea/DTT, the "311" mouse monoclonal antibody, which recognizes the three chains α, β and weakly, γ of human fibrinogen and fibrin, is mainly reactive with respect to the w64-78 and w55-61 antigens. Similarly, two antisera, one from sheep and the other from rabbit, directed, respectively, against recombinant α- and β-chains of fibrinogen, recognized mainly a protein which co-migrates with the w64-78 antigen and a protein which co-migrates with the w55-61 antigen, respectively.

EXAMPLE 2

Reactivity of Rheumatoid Sera and of Purified AFAS with Deiminated Fibrinogen In Vitro The reactivity with respect to deiminated and nondeiminated fibrinogen was studied by immunotransfer. The following were used: the purified AFA fractions, 37 AFA-positive rheumatoid sera of decreasing titer, 10 AFA-negative rheumatoid sera and 19 AFA-negative sera derived from patients suffering from forms of inflammatory or non-inflammatory rheumatism (AFA titers determined by immunotransfer on epidermal extracts enriched in filaggrin acid variant).

The results are illustrated by FIG. 3A in the case of nondeiminated fibrinogen and by FIG. 3B in the case of deiminated fibrinogen.

Legend to FIG. 3:

FIG. 3A: non deiminated purified human fibrinogen;
311=antifibrinogen monoclonal antibody 311;
control sera=sera derived from patients suffering from forms of inflammatory rheumatism other than RA, or from healthy donors;
RA sera=rheumatoid sera;
*AFA+=AFA-positive;
*AFA−=AFA-negative;
FIG. 3B: purified human fibrinogen deiminated with a PAD;
311=antifibrinogen monoclonal antibody 311;
C1=sheep antibody directed against mouse IgGs;
C2=sheep antibody directed against protein A;
control sera=sera derived from patients suffering from forms of inflammatory rheumatism other than RA, or from healthy donors;
RA sera=rheumatoid sera;
AFA+=AFA-positive;
AFA−=AFA-negative;

Nondeiminated Fibrinogen

After separation by SDS-PAGE, under the conditions described in example 1 above, the nondeiminated fibrinogen is composed of 3 polypeptides having respective apparent molecular weights 48 kDa, 58 kDa and 69 kDa, corresponding to the expected apparent molecular masses of the α-, β- and γ-polypeptide chains making up the protein (results not given). The "311" antifibrinogen monoclonal antibody strongly recognizes the α- and β-polypeptide chains and very weakly the γ-polypeptide chain (FIG. 3A).

Antisera specific for each of the α-, β- and γ-chains of fibrinogen also showed reactivity with respect to the chain against which they were respectively directed (results not shown).

Deimination of the Fibrinogen

A peptidyl arginine deiminase (PAD) purified from rabbit skeletal muscle (Sigma, St. Louis, Mo.) was used. The human fibrinogen (Calbiochem, San Diego, Calif.) was incubated at the concentration of 0.86 mg/ml, in the presence or absence of PAD (7 U/mg of protein) for 2 h at 50° C., in 0.1 M Tris-HCl buffer, pH 7.4, containing 10 mM of $CaCl_2$ and 5 mM of DTT. These conditions are those which previously made it possible to generate the epitopes on a human recombinant filaggrin, recognized by AFAs [GIRBAL-NEUHAUSER et al., J. Immunol., 162, 585 594 (1999)]. The deimination was then stopped by adding 2% of SDS and heating at 100° C. for 3 min.

After deimination for 2 hours, the electrophoretic mobility by SDS-PAGE of the two α- and β-polypeptides became modified and that of the γ-polypeptide remained unchanged. Specifically, the protein corresponding to the α-chain then appeared in the form of a diffuse band of 82 to 95 kDa and was immunodetected by both the "31" antifibrinogen monoclonal antibody (FIG. 3B) and the antiserum directed against the α-chain of fibrinogen (results not shown).

The protein corresponding to the β-chain appeared in the form of a well-defined doublet with the molecular weight of 458 kD for the lower band and 60 kD for the upper band, which was not recognized by the "311" antifibrinogen monoclonal antibody (FIG. 3B) but was immunodetected by the rabbit antiserum directed against the recombinant β-chain of human fibrinogen (results not shown).

No reactivity for the α-chain or for the β-chain is observed with the C1 and C2 antibodies.

Reactivity of the Sera

The reactivity of the sera with respect to the α- and β-chains of nondeiminated fibrinogen proved to be zero or very weak and concerned only a few sera rarely occurring, belonging to no particular subgroup.

On the other hand, after deimination, the polypeptides corresponding to the deiminated α- and β-chains react strongly with the purified AFAs (results not shown) and with all of the 37 AFA-positive rheumatoid sera (with the exception of that which has the lowest AFA titer). Moreover, 6 AFA-negative rheumatoid sera out of 10 also clearly recognized the deiminated α- or β-polypeptides: 2 immunodetected the α-polypeptide and the β-polypeptide doublet, 3 others only detected the β-polypeptide doublet, and only 1 immunodetected exclusively the α-polypeptide. On the other hand, with the exception of a serum derived from a patient suffering from Sjogren's syndrome, which was reactive on the β-polypeptide doublet, none of the control sera immunodetected the deiminated fibrinogen.

The affinity of the AFA-positive rheumatoid sera with respect to the two deiminated α- and β-polypeptides proved to be slightly variable from one serum to the other. Thus, 6 sera, while strongly detecting the β-polypeptide, only very weakly recognized the α-polypeptide. Similarly, 3 sera, highly reactive with respect to the α-polypeptide, did not detect the deiminated β-polypeptide. Moreover, the intensity of labeling of the two polypeptides appears, overall, to be proportional to the AFA titer of the sera. It should be noted that the sera reactive on the deiminated a and β-polypeptides of fibrinogen were also reactive with respect to high molecular weight (greater than 200 kD) polypeptides generated during the deimination of the fibrinogen. These polypeptides which clearly react with the antifibrinogen antibodies are very probably fibrinogen chain aggregates.

In conclusion, recognition of the α- and β-polypeptides of fibrinogen by rheumatoid sera is not only entirely dependent on their deimination, since the nondeiminated polypeptides are never recognized, but it is also clearly linked to the antifilaggrin reactivity of these sera. It should be noted that these deiminated polypeptides make it possible to detect with great sensitivity the AFAs present in rheumatoid sera.

These results clearly demonstrate that the antigenic targets of the ASAs in rheumatoid synovial joints are deiminated forms of the α-chain and of the β-chain of human fibrin.

The invention claimed is:

1. A purified citrullinated polypeptide which reacts with rheumatoid arthritis-specific anti-filaggrin autoantibodies, and is selected from the group consisting of:
    a) a citrullinated β chain of a human fibrin;
    b) a citrullinated polypeptide resulting from the action of peptidyl arginine deiminase on an β-chain of a human fibrinogen; and
    c) a fragment of a citrullinated β-chain of human fibrin consisting of at least 5 consecutive amino acids of a) and which also comprises at least one citrulline residue.

2. An antigenic composition for diagnosing the presence of rheumatoid arthritis-specific anti-filaggrin autoantibodies in a biological sample, comprising at least one citrullinated polypeptide as claimed in claim 1, optionally labeled with or conjugated to a carrier molecule.

3. A kit for detecting rheumatoid arthritis-specific anti-filaggrin autoantibodies in a biological sample, comprising a polypeptide as claimed in claim 1 or a combination thereof, and buffers and reagents suitable for constituting a reaction medium which allows the formation of an antigen/antibody complex.

4. The antigenic composition according to claim 2, wherein said citrullinated polypeptide is labeled.

5. The antigenic composition according to claim 2, wherein said citrullinated polypeptide is conjugated to a carrier molecule.

6. The purified citrullinated polypeptide according to claim 1, which is a).

7. The purified citrullinated polypeptide according to claim 1, which is b).

8. The purified citrullinated polypeptide according to claim 1, which is c).

9. The antigenic composition according to claim 2, wherein said citrullinated polypeptide is a).

SEQUENCE LISTING

```
<160> NUMBER OF SEQ ID NOS: 2

<210> SEQ ID NO 1
<211> LENGTH: 11
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 1

Gly Pro Arg Val Val Glu Arg His Gln Ser Ala
1               5                   10

<210> SEQ ID NO 2
<211> LENGTH: 9
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 2

Gly His Arg Pro Leu Asp Lys Lys Arg
1               5
```

10. The antigenic composition according to claim 2, wherein said citrullinated polypeptide is b).

11. The antigenic composition according to claim 2, wherein said citrullinated polypeptide is c).

12. The kit according to claim 3, which further comprises reagents for detecting said antigen/antibody complex.

13. A method for detecting rheumatoid arthritis specific anti-filaggrin autoantibodies in a biological sample, which method comprises:

contacting said biological sample with a polypeptide as claimed in claim 1 or a combination thereof, wherein the formation of an antigen/antibody complex is indicative of the presence of rheumatoid arthritis-specific anti-filaggrin autoantibodies; and detecting the antigen/antibody complex possibly formed.

14. The method according to claim 13, wherein said citrullinated polypeptide is a).

15. The method according to claim 13, wherein said citrullinated polypeptide is b).

16. The method according to claim 13, wherein said citrullinated polypeptide is c).

* * * * *